United States Patent [19]

Drabek et al.

[11] Patent Number: 4,971,994
[45] Date of Patent: Nov. 20, 1990

[54] THIOUREAS

[75] Inventors: Jozef Drabek, Oberwil, Switzerland; Manfred Böger, Weil am Rhein, Fed. Rep. of Germany; Josef Ehrenfreund, Allschwil, Switzerland

[73] Assignee: Ciba-Geigy Corporation, Ardsley, N.Y.

[21] Appl. No.: 336,398

[22] Filed: Apr. 11, 1989

[30] Foreign Application Priority Data

Apr. 20, 1988 [CH] Switzerland ............... 1450/88
May 5, 1988 [CH] Switzerland ............... 1690/88

[51] Int. Cl.$^5$ ............... A01N 47/10; C07C 321/00
[52] U.S. Cl. ............... 514/480; 514/481; 514/482; 514/584; 560/10; 560/13; 560/16; 564/23
[58] Field of Search ............... 560/10, 13, 16; 564/23; 514/480, 481, 482, 584

[56] References Cited

U.S. PATENT DOCUMENTS

| | | | |
|---|---|---|---|
| 4,194,008 | 3/1980 | Enders et al. | 424/322 |
| 4,908,383 | 3/1990 | Drabek et al. | 514/485 |

FOREIGN PATENT DOCUMENTS

| | | | |
|---|---|---|---|
| 0278673 | 8/1988 | European Pat. Off. | 564/23 |
| 767161 | 5/1970 | France | 564/23 |
| 55-89260 | 7/1980 | Japan . | |
| 87/9395 | 8/1988 | South Africa . | |
| 506505 | 6/1971 | Switzerland . | |

OTHER PUBLICATIONS

Pratt et al. J. Am Chem. Soc. 94 2823ff (1972).
Kawalek et al. Ca Czech Chem. Commun 50 766ff (1985).
Dixon, J. Chem. Soc. 83, 550ff (1903).
Dixon et al. J. Chem. Soc. 91 122ff (1907).
Toldy et al. Acta Chemica Academiae Scierruarum Hugaricae, 69 221ff (1971).

*Primary Examiner*—Bruce Gray
*Attorney, Agent, or Firm*—Kevin T. Mansfield; Edward McC. Roberts

[57] ABSTRACT

Novel N-phenyl-N-carbonylthioureas of the formula I

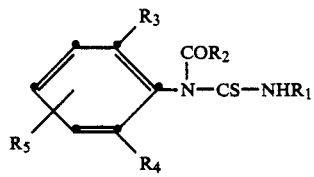

in which
$R_1$ is $C_1$-$C_{10}$alkyl, phenyl-$C_1$-$C_7$alkyl; $C_1$-$C_{10}$alkyl or phenyl-$C_1$-$C_7$alkyl each of which is monohalogenated or polyhalogenated or interrupted once or more than once by oxygen and/or sulfur; $C_3$-$C_8$cycloalkyl; C hd 3-$C_8$cycloalkyl which is monosubstituted or polysubstituted by halogen or $C_1$-$C_5$alkyl; or $C_3$-$C_8$-cycloalkyl-$C_1$-$C_4$alkyl,
$R_2$ is $C_1$-$C_{10}$alkyl, $C_2$-$C_{10}$alkenyl, $C_2$-$C_{10}$alkynyl, phenyl, phenyl-$C_1$-$C_7$alkyl, $C_3$-$C_8$cycloalkyl; $C_1$14 $C_{10}$alkyl, $C_2$-$C_{10}$alkenyl, $C_2$-$C_{10}$alkynyl or phenyl-$C_1$-$C_7$alkyl each of which is monohalogenated or polyhalogenated or interrupted once or more than once by oxygen and/or sulfur; $C_3$-$C_8$cycloalkyl; phenyl or $C_3$-$C_8$cycloalkyl each of which is monosubstituted or polysubstituted by halogen or $C_1$-$C_5$alkyl; or is a radical —$OR_9$;
$R_3$ is $C_1$-$C_{10}$alkyl, $C_1$-$C_{10}$alkoxy, $C_3$-$C_7$cycloalkyl or $C_5$-$C_6$cycloalkenyl;
$R_4$ is $C_1$-$C_7$cycloalkyl or $C_5$-$C_6$-cycloalkenyl;
$R_5$ is hydrogen or $R_6(Y)_n$;
$R_6$ is $C_1$-$C_{10}$alkyl, phenyl, naphthyl, indanyl, tetrahydronaphthyl; or phenyl, naphthyl, indanyl or tetrahydronaphthyl each of which is monosubstituted or polysubstituted by ahlogen, $C_1$-$C_4$alkyl, $C_1$-$C_4$alkoxy, $C_1$-$C_4$haloalkyl or $C_1$-$C_4$haloalkoxy;
$R_9$ is $C_1$-$C_{10}$alkyl, $C_3$-$C_{10}$alkenyl, $C_3$-$C_{10}$alkynyl, phenyl, phenyl-$C_1$-$C_7$alkyl, $C_3$-$C_8$cycloalkyl; $C_1$-$C_{10}$alkyl, $C_3$-$C_{10}$alkenyl, $C_3$-$C_{10}$alkynyl, phenyl-$C_1$-$C_7$alkyl each of which is monohalogenated or polyhalogenated or interrupted once or more than once by oxygen and/or sulfur; or phenyl or $C_3$-$C_8$cycloalkyl each of which is monosubstituted or polysubstituted by halogen or $C_1$-$C_5$alkyl;
Y is O, S, SO, $SO_2$, NH, N(CHO), N($CH_3$) or C($R_7$)$R_8$, where $R_7$ and $R_8$ each are hydrogen or $C_1$-$C_4$alkyl; and
n is 0 or 1 with the proviso that $R_2$ can stand for the radical —$OR_9$ only when $R_5$ is other than hydrogen and $C_1$-$C_{10}$alkoxy; processes and salts of corresponding isothioureas as intermediates for their preparation, their use in the control of pests, and also pesticides containing at least one compound of the formula I or an active intermediate are disclosed. The preferred field of application is the control of pests on animals and plants.

10 Claims, No Drawings

THIOUREAS

The present invention relates to novel substituted N-phenyl-N-acylthioureas and N-phenyl-N-carboxylthioureas, processes and intermediates for their preparation, pesticides containing these compounds, and their use in the control of pests.

The compounds according to the invention are those of the formula I

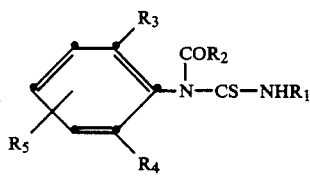

in which
$R_1$ is $C_1$–$C_{10}$alkyl, phenyl-$C_1$–$C_7$alkyl; $C_1$–$C_{10}$alkyl or phenyl-$C_1$–$C_7$alkyl each of which is monohalogenated or polyhalogenated or interrupted once or more than once by oxygen and/or sulfur; $C_3$–$C_8$cycloalkyl; $C_3$–$C_8$cycloalkyl which is monosubstituted or polysubstituted by halogen or $C_1$–$C_5$-alkyl; or $C_3$–$C_8$-cycloalkyl-$C_1$–$C_4$alkyl, $R_2$ is $C_1$–$C_{10}$alkyl, $C_2$–$C_{10}$alkenyl, $C_2$–$C_{10}$alkynyl, phenyl, phenyl-$C_1$–$C_7$-alkyl, $C_3$–$C_8$cycloalkyl; $C_1$–$C_{10}$alkyl, $C_2$–$C_{10}$alkenyl, $C_2$–$C_{10}$alkynyl or phenyl-$C_1$–$C_7$alkyl each of which is monohalogenated or polyhalogenated or interrupted once or more than once by oxygen and/or sulfur; $C_3$–$C_8$cycloalkyl; phenyl or $C_3$–$C_8$cycloalkyl each of which is monosubstituted or $R_3$ is $C_1$–$C_{10}$alkyl, $C_1$–$C_{10}$alkoxy, $C_3$–$C_7$cycloalkyl or $C_5$–$C_6$cycloalkenyl;

$R_4$ is $C_1$–$C_{10}$alkyl, $C_3$–$C_7$cycloalkyl or $C_5$–$C_6$cycloalkenyl;

$R_5$ is hydrogen or $R_6(Y)_n$;

$R_6$ is $C_1$–$C_{10}$alkyl, phenyl, naphthyl, indanyl, tetrahydronaphthyl; or phenyl, naphthyl, indanyl or tetrahydronaphthyl each of which is monosubstituted or polysubstituted by halogen, $C_1$–$C_4$alkyl, $C_1$–$C_4$alkoxy, $C_1$–$C_4$haloalkyl or $C_1$–$C_4$haloalkoxy;

$R_9$ is $C_1$–$C_{10}$alkyl, $C_3$–$C_{10}$alkenyl, $C_3$–$C_{10}$alkynyl, phenyl, phenyl-$C_1$–$C_7$alkyl, $C_3$–$C_8$cycloalkyl; $C_1$–$C_{10}$alkyl, $C_3$–$C_{10}$alkenyl, $C_3$–$C_{10}$alkynyl, phenyl-$C_1$–$C_7$alkyl each of which is monohalogenated or polyhalogenated or interrupted once or more than once by oxygen and/or sulfur; or phenyl or $C_3$–$C_8$cycloalkyl each of which is monosubstituted or polysubstituted by halogen or $C_1$–$C_5$alkyl;

Y is O, S, SO, $SO_2$, NH, N(CHO), N($CH_3$) or C($R_7$)$R_8$, where $R_7$ and $R_8$ each are hydrogen or $C_1$–$C_4$alkyl; and n is 0 or 1 with the proviso that $R_2$ can stand for the radical $-OR_9$ only when $R_5$ is other than hydrogen and $C_1$–$C_{10}$alkoxy; processes and salts of corresponding isothioureas as intermediates for their preparation, their use in the control of pests, and also pesticides containing at least one compound of the formula I or an active intermediate are disclosed. The preferred field of application is the control of pests on animals and plants.

Halogens which are suitable as substituents are fluorine and chlorine, and also bromine and iodine, fluorine and chlorine being preferred.

The alkyl and alkoxy radicals which are suitable as substituents can be straight-chain or branched. Examples of such alkyls are, inter alia, methyl, ethyl, propyl, isopropyl, butyl, isobutyl, sec-butyl, tert-butyl or pentyl, hexyl, octyl and their isomers. Alkoxy radicals which are suitable and which may be mentioned are, inter alia, methoxy, ethoxy, propoxy, isopropoxy or butoxy and their isomers.

The alkenyls and alkynyls which are suitable as substituents can be straight-chain or branched and can contain one or more unsaturated bonds, in which case double and triple bonds can occur in the same radical. Preferably, these unsaturated radicals contain two to six carbon atoms. Examples of such alkenyls and alkynyls are, inter alia, vinyl, allyl, 1-propenyl, isopropenyl, allenyl, butenyls, butadienyls, hexenyls, hexanedienyls, ethynyl, 1-propynyl, 2-propynyl, butynyls, pentynyls, hexynyls, hexadiynyls, 2-penten-4-ynyl.

The phenylalkyls which are suitable as substituents can be straight-chain or branched. Suitable examples are, inter alia, benzyl, phenethyl, phenpropyl, phenisopropyl, phenbutyl and its isomers.

If the alkyls, alkoxyls, alkenyls, alkynyls or phenylalkyls which are suitable as substituents are substituted by halogen, they can be only partly nucleus halogenated or alternatively perhalogenated. The phenylalkyls can be substituted by halogen both in the phenyl and in the alkyl chain, or simultaneously in both, in which case the above definitions apply to the halogens, alkyls, alkoxyls, alkenyls,alkynyls and phenylalkyls. Examples of such groups are, inter alia, methyl which is monosubstituted to trisubstituted by fluorine, chlorine and/or bromine, for example $CHF_2$ or $CF_3$; ethyl which is monosubstituted to pentasubstituted by fluorine, chlorine and/or bromine, for example $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl each of which is monosubstituted to heptasubstituted by fluorine, chlorine and/or bromine, for example $CH_2CHBrCH_2Br$, $CF_2CHFCF_3$, $CH_2CF_2CF_3$ or $CH(CF_3)_2$; butyl or one of its isomers each of which is monosubstituted to nonasubstituted by fluorine, chlorine, and/or bromine, for example $CF(CF_3)CHFCF_3$ or $CH_2(CF_2)_2CF_3$; vinyl, propynyl or pentadiynyl each of which is monosubstituted to trisubstituted by fluorine, chlorine and/or bromine; allyl, 1-propenyl, butadienyl or a butynyl each of which is monosubstituted to pentasubstituted by fluorine, chlorine and/or bromine; butenyl, pentadienyl or pentynyl each of which is monosubstituted to heptasubstituted by fluorine, chlorine and/or bromine; benzyl which is monosubstituted to heptasubstituted by fluorine, chlorine and/or bromine; phenethyl which is monosubstituted to nonasubstituted by fluorine, chlorine and/or bromine; phenpropyl or phenisopropyl each of which is monosubstituted to undecasubstituted by fluorine, chlorine and/or bromine.

The alkyls, alkenyls, alkynyls and phenylalkyls which are interrupted by oxygen and/or sulfur, which are suitable as substituents, can be simple ethers or polyalkylene glycols or polyalkylene thioglycols, in which case chains which simultaneously contain oxygen and sulfur are also possible. Examples are, inter alia, radicals, such as methoxymethyl, methylthiomethyl, methoxymethoxymethyl, methoxyethyl, ethoxyethyl, ethylthioethyl, vinyloxymethyl, allylthioethyl, methoxypropynyl, benzoxymethyl, benzylthioethyl.

Examples of the cycloalkyls and cycloalkenyls, which are suitable as substituents, are cyclopropyl, cyclobutyl, cyclopentyl, 2-cyclopenten-1-yl, cyclohexyl or cyclohexenyl. These radicals can be monosubstituted or polysubstituted by halogen or alkyl, for example 2-chlorocyclopropyl, 2,2-dimethylcyclopropyl, 3- chlorocyclobutyl, 2-methylcyclohexyl, 2,4-dimethylcyclohexyl, 2,4,6-trimethylcyclohexyl, and/or can be linked to the remainder of the molecule via a $C_1$-$C_4$alkylene bridge, for example 1-cyclopropylethyl.

Two sub-groups from the compounds of the formula I must be emphasized. One is that of the formula Ia

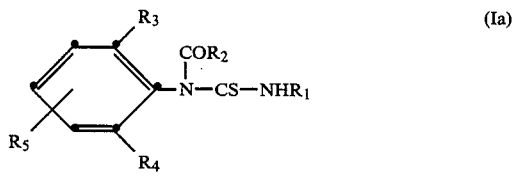

in which $R_1$ is $C_1$-$C_{10}$alkyl, phenyl-$C_1$-$C_7$alkyl; $C_1$-$C_{10}$alkyl or phenyl-$C_1$-$C_7$alkyl each of which is monohalogenated or polyhalogenated or interrupted once or more than once by oxygen and/or sulfur; $C_3$-$C_8$cycloalkyl; or $C_3$-$C_8$cycloalkyl which is monosubstituted or polysubstituted by halogen or $C_1$-$C_5$alkyl;

$R_2$ is $C_1$-$C_{10}$alkyl, $C_2$-$C_{10}$alkenyl, $C_2$-$C_{10}$alkynyl, phenyl, phenyl-$C_1$-$C_7$alkyl, or is $C_1$-$C_{10}$alkyl, or is $C_2$-$C_{10}$alkenyl, $C_2$-$C_{10}$alkenyl or phenyl-$C_1$-$C_7$alkyl each of which is monohalogenated or polyhalogenated or interrupted once or more than once by oxygen and/or sulfur; $C_3$-$C_8$cycloalkyl; or $C_3$-$C_8$cycloalkyl which is monosubstituted or polysubstituted by halogen or $C_1$-$C_5$alkyl;

$R_3$ is $C_1$-$C_{10}$alkyl, $C_1$-$C_{10}$alkoxy, $C_3$-$C_7$cycloalkyl or $C_5$-$C_6$cycloalkenyl;

$R_4$ is $C_1$-$C_{10}$alkyl, $C_3$-$C_7$cycloalkyl or $C_5$-$C_6$cycloalkenyl;

$R_5$ is hydrogen or $R_6(Y)_n$;

$R_6$ is $C_1$-$C_{10}$alkyl, phenyl, naphthyl, indanyl, tetrahydronaphthyl; or phenyl, naphthyl, indanyl or tetrahydronaphthyl each of which is monosubstituted or polysubstituted by halogen, $C_1$-$C_4$alkyl, $C_1$-$C_4$alkoxy, $C_1$-$C_4$haloalkyl or $C_1$-$C_4$haloalkoxy;

Y is O, S, SO, $SO_2$, NH, N(CHO), $N(CH_3)$ or $C(R_7)R_8$, where $R_7$ and $R_8$ each are hydrogen or $C_1$-$C_4$alkyl; and n is 0 or 1.

The second comes under the formula Ib

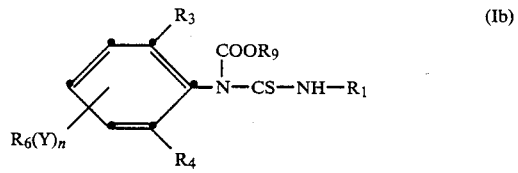

in which $R_1$ is $C_1$-$C_{10}$alkyl, phenyl-$C_1$-$C_7$alkyl; $C_1$-$C_{10}$alkyl or phenyl-$C_1$-$C_7$alkyl each of which is monohalogenated or polyhalogenated or interrupted once or more than once by oxygen and/or sulfur; $C_3$-$C_8$cycloalkyl; $C_3$-$C_8$cycloalkyl which is monosubstituted or polysubstituted by halogen or $C_1$-$C_5$alkyl; or $C_3$-$C_8$cycloalkyl-$C_1$-$C_4$alkyl;

$R_3$ is $C_1$-$C_{10}$alkyl, $C_1$-$C_{10}$alkoxy, $C_3$-$C_7$cycloalkyl or $C_5$-$C_6$cycloalkenyl;

$R_4$ is $C_1$-10alkyl, $C_3$-$C_7$cycloalkyl or $C_5$-$C_6$cycloalkenyl;

$R_6$ is phenyl, naphthyl, indanyl, tetrahydronaphthyl; or phenyl, naphthyl, indanyl or tetrahydronaphthyl each of which is monosubstituted or polysubstituted by halogen, $C_1$-$C_4$alkyl, $C_1$-$C_4$alkoxy, $C_1$-$C_4$haloalkyl or $C_1$-$C_4$haloalkoxy;

$R_9$ is $C_1$-$C_{10}$alkyl, $C_3$-$C_{10}$alkenyl, $C_3$-$C_{10}$alkynyl, phenyl, phenyl-$C_1$-$C_7$alkyl, $C_3$-$C_8$cycloalkyl; $C_1$-$C_{10}$alkyl, $C_3$-$C_{10}$alkenyl, $C_1$-$C_{alkynyl}$, phenyl-$C_1$-$C_7$alkyl each of which is monohalogenated or polyhalogenated or interrupted once or more than once by oxygen and/or sulfur; or is phenyl or $C_3$-$C_8$cycloalkyl each of which is monosubstituted or polysubstituted by halogen or $C_1$-$C_5$alkyl;

Y is O, S, SO, $SO_2$, NH, N(CHO), $N(CH_3)$ or $C(R_7)R_8$, where $R_7$ and $R_8$ each are hydrogen or $C_1$-$C_4$alkyl; and n is 0 or 1.

Important compounds of the formula Ia are those in which $R_1$ is $C_1$-$C_5$alkyl or phenyl-$C_1$-$C_3$alkyl; $R_2$ is $C_1$-$C_5$alkyl, $C_2$-$C_5$alkenyl, $C_2$-$C_5$alkynyl, phenyl or phenyl-$C_1$-$C_3$alkyl; $R_3$ is $C_1$-$C_5$alkyl, $C_1$-$C_5$alkoxy, cyclopentyl or cyclopentenyl; $R_4$ is $C_1$-$C_5$alkyl; $R_5$ is hydrogen or $R_6(Y)_n$; $R_6$ is $C_1$-$C_5$alkyl, phenyl, naphthyl or indanyl; or is phenyl, naphthyl or indanyl each of which is monosubstituted or polysubstituted by fluorine, chlorine or $C_1$-$C_3$alkyl; Y is O, S, $SO_2$, NH, N(CHO), $N(CH_3)$ or $C(R_7)R_8$, where $R_7$ and $R_8$ each are hydrogen or methyl; and n is 0 or 1.

Preferred compounds of the formula Ia are those in which $R_1$ is $C_3$-$C_5$alkyl or phenyl-$C_2$-$C_3$alkyl; $R_2$ is $C_1$-$C_3$alkyl or phenyl; $R_3$ is $C_1$-$C_4$alkyl, $C_1$-$C_4$alkoxy, cyclopentyl or cyclopentenyl; $R_4$ is $C_1$-$C_4$alkyl; $R_5$ is hydrogen or $R_6Y$ in the 4-position; $R_6$ is $C_1$-$C_4$alkyl, phenyl or phenyl which is substituted by 1 to 2 fluorine; and Y is O or S.

Important compounds of the formula Ib are those in which $R_1$ is $C_1$-$C_5$alkyl or phenyl-$C_1$-$C_3$alkyl; $R_3$ is $C_1$-$C_5$alkyl, $C_1$-$C_5$alkoxy, cyclopentyl or cyclopentenyl; $R_4$ is $C_1$-$C_5$alkyl; $R_6$ is phenyl, naphthyl or indanyl; $R_9$ is $C_1$-$C_5$alkyl, $C_3$-$C_5$alkenyl, $C_3$-$C_5$alkynyl, phenyl or phenyl-$C_1$-$C_3$alkyl; Y is O, S, $SO_2$, NH, N(CHO), $N(CH_3)$ or $C(R_7)R_8$, where $R_7$ and $R_8$ each are hydrogen or methyl; and n is 0 or 1.

Preferred compounds of the formula Ib are those in which $R_1$ is $C_3$-$C_5$alkyl or phenyl-$C_2$-$C_3$alkyl; $R_3$ is $C_1$-$C_4$alkyl, $C_1$-$C_4$alkoxy, cyclopentyl; $R_4$ is $C_1$-$C_4$alkyl; $R_6$ is phenyl or phenyl which is substituted by 1 to 2 fluorine; $R_9$ is $C_1$-$C_3$alkyl or phenyl; Y in the 4-position is O or S; and n is 1.

The compounds of the formula I according to the invention can be prepared by processes which are known in principle, for example by (a) reacting a thiourea of the formula II

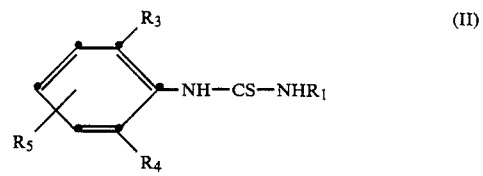

with an acyl halide of the formula III

XCOR₂ (III)

in a solvent and in the presence of a base under atmospheric pressure at −30° to +100° C., or (b) hydrolysing a salt of an isothiourea of the formula IV

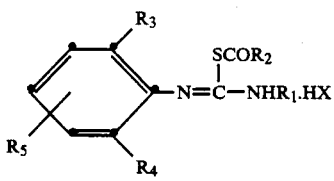

at room temperature in an aqueous solution. In formulae II to IV, $R_1$, $R_2$, $R_3$, $R_4$ and $R_5$ are as defined in formula I and X is the radical of a hydrohalic acid, in particular chlorine.

Suitable solvents are solvents and diluents which are inert towards the reactants, for example ethers or ether-like compounds, such as, inter alia, diethyl ether, diisopropyl ether, dioxane or tetrahydrofuran; aromatic hydrocarbons, such as benzene, toluene or xylenes; ketones, such as acetone, methyl ethyl ketone or cyclohexanone; nitriles, such as acetonitrile; halohydrocarbons, such as chloroform or methylene chloride; or dimethylformamide.

Bases which are suitable can be of organic or inorganic origin, for example sodium hydride, sodium carbonate, potassium carbonate or calcium carbonate, or tertiary amines, such as triethylamine, triethylenediamine or 4-dimethylaminopyridine or pyridine.

The thioureas of the formula II, in turn, can be prepared by processes which are known in principle, for example by reacting an isothiocyanate of the formula V

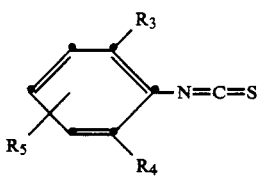

with an amine of the formula VI $$H_2N-R_1 \quad (VI)$$

where, in formulae V and VI, $R_1$, $R_3$, $R_4$ and $R_5$ are as defined in formula I.

The process for the preparation of compounds of the formula II is expediently carried out in the presence of a solvent or diluent which is inert towards the reactants, at a reaction temperature of 0° to +100° C. under atmospheric pressure. Solvents and diluents which are suitable have been mentioned already, for example for the process for the preparation of the compounds of the formula I.

The salts of the isothioureas of the formula IV can be prepared by processes which are known in principle, for example by reacting a thiourea of the formula II with an acyl halide of the formula III in a solvent under atmospheric pressure at a temperature of −20° to +100° C., in which case the reaction with an acyl chloride is particularly preferred.

The compounds of the formula IV are novel, and, as intermediates, also form a subject-matter of the present invention. In contrast, the compounds of the formulae II, III, V and VI are known and can be prepared by processes known in principle.

It has now been found that the compounds of the formula I according to the invention and the intermediates of the formula IV are valuable active substances in pest control while being well tolerated by warm-blooded animals, fish and plants. For example, the compounds of the formulae I and IV are suitable for controlling pests on animals and plants. Such pests mainly belong to the phylum of the arthropods, such as, in particular, insects of the orders of the Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, and arachnids of the order of the Acarina, for example mites and ticks, in which case each of the developmental stages of the pests can be controlled, i.e., the adults, pupae and nymphs, and also in particular the larvae and eggs. In this way, it is possible to effectively control larvae and eggs of phytopathogenic noxious insects and noxious mites in decorative and commercial plantings, for example in fruit and vegetable plantings, but also sucking insects, for example rice leaf hoppers and aphids, and soil insects, for example Diabrotica species in maize crops. If compounds of the formulae I and IV are taken up by imagines, their effect can be seen from the immediate destruction of the pests, or alternatively, in laying a reduced number of eggs, and/or in a reduced hatching rate. The latter phenomenon can be observed in particular in the case of Coleoptera. In the control of pests which parasitize animals, in particular domestic animals and productive livestock, the reactive substances are particularly suitable for ectoparasites, for example mites and ticks, and Diptera, for example Lucilia sericata. Moreover, the compounds of the formula I and its intermediates of the formula IV show a considerable microbicidal action, which means that mainly plant-pathogenic fungi of the class of the Oomycetidae, for example families of the order of the Peronosporales (Plasmopara sp.) can be controlled with a lasting effect.

The sub-group from the compounds of the formula IV which must be emphasized is that of the formula IVa

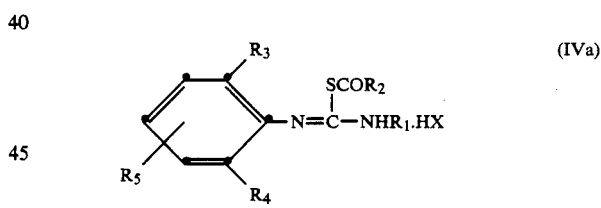

in which
$R_1$ is $C_1$-$C_{10}$alkyl, phenyl-$C_1$-$C_7$alkyl; $C_1$-$C_{10}$alkyl or phenyl-$C_1$-$C_7$alkyl each of which is monohalogenated or polyhalogenated or interrupted once or more than once by oxygen and/or sulfur; $C_3$-$C_8$cycloalkyl; or $C_3$-$C_8$cycloalkyl which is monosubstituted or polysubstituted by halogen or $C_1$-$C_5$alkyl;

$R_2$ is $C_1$alkyl, $C_2$-$C_{10}$alkenyl, $C_2$-$C_{10}$alkynyl, phenyl, phenyl-$C_1$-$C_7$alkyl; $C_1$-$C_{10}$alkyl, $C_2$-$C_{10}$alkenyl, $C_2$-$C_{10}$alkynyl or phenyl-$C_1$-$C_7$alkyl each of which is monohalogenated or polyhalogenated or interrupted once or more than once by oxygen and/or sulfur; $C_3$-$C_8$cycloalkyl; or $C_3$-$C_8$cycloalkyl which is monosubstituted or polysubstituted by halogen or $C_1$-$C_5$alkyl;

$R_3$ is $C_1$-$C_{10}$alkyl, $C_1$-$C_{10}$alkoxy, $C_3$-$C_7$cycloalkyl or $C_5$-$C_6$cycloalkenyl;

$R_4$ is $C_1$-$C_{10}$alkyl, $C_3$-$C_7$cycloalkyl or $C_5$-$C_6$cycloalkenyl;

$R_5$ is hydrogen or $R_6(Y)_n$;

$R_6$ is $C_1$–$C_{10}$alkyl, phenyl, naphthyl, indanyl, tetrahydronaphthyl; or phenyl, naphthyl, indanyl or tetrahydronaphthyl each of which is monosubstituted or polysubstituted by halogen, $C_1$–$C_4$alkyl, $C_1$–$C_4$alkoxy, $C_1$–$C_4$haloalkyl or $C_1$–$C_4$haloalkoxy;

Y is O, S, SO, $SO_2$, NH, N(CHO), N($CH_3$) or C($R_7$)$R_8$, where $R_7$ and $R_8$ each are hydrogen or $C_1$–$C_4$alkyl; and n is 0 or 1, and X is the radical of a hydrohalic acid.

Preferred compounds of the formula VIa are those in which $R_1$ is $C_1$–$C_5$alkyl or phenyl-$C_1$–$C_3$alkyl; $R_2$ is $C_1$–$C_5$alkyl, $C_2$–$C_5$alkenyl, $C_2$–$C_5$alkynyl, phenyl or phenyl-$C_1$–$C_3$alkyl; $R_3$ is $C_1$–$C_5$alkyl, $C_1$–$C_5$alkoxy, cyclopentyl or cyclopentenyl; $R_4$ is $C_1$–$C_5$alkyl; $R_5$ is hydrogen or $R_6(Y)_n$; $R_6$ is $C_1$–$C_5$alkyl, phenyl, naphthyl or indanyl; or phenyl, naphthyl or indanyl each of which is monosubstituted or polysubstituted by fluorine, chlorine or $C_1$–$C_3$alkyl; Y is O, S, $SO_2$, NH, N(CHO), N($CH_3$) or C($R_7$)$R_8$, where $R_7$ and $R_8$ each are hydrogen or methyl; and n is 0 or 1, and X is the radical of a hydrohalic acid.

Very particularly noticeable, however, are those compounds of the formula IVa in which $R_1$ is $C_3$–$C_5$alkyl or phenyl-$C_2$–$C_3$alkyl; $R_2$ is $C_1$–$C_3$alkyl or phenyl; $R_3$ is $C_1$–$C_4$alkyl, $C_1$–$C_4$alkoxy, cyclopentyl or cyclopentenyl; $R_4$ is $C_1$–$C_4$alkyl; $R_5$ is hydrogen or $R_6Y$ in the 4-position; $R_6$ is $C_1$–$C_4$alkyl, phenyl or phenyl which is substituted by 1 or 2 fluorine; and Y is O or S; and X is chlorine.

The good pesticidal action of the compounds of the formulae I and IV according to the invention corresponds to a destruction rate (mortality) of at least 50–60% of the mentioned pests.

By adding other insecticides and/or acaricides, the action of the compounds according to the invention, or of the agents containing them, can be considerably broadened and adapted to given circumstances. Examples of suitable additives are representatives of the following classes of active substances: organic phosphorus compounds, nitrophenols and derivatives, formamidines, ureas, carbamates, pyrethroids, chlorinated hydrocarbons and preparations of *Bacillus thuringiensis*.

The compounds of the formulae I and IV are employed as such or preferably together with auxiliaries conventionally used in the art of formulation, and they can therefore be processed in a known manner, for example to emulsion concentrates, directly sprayable or dilutable solutions, diluted emulsions, wettable powders, soluble powders, dusts, granules, and also encapsulations, for example in polymeric substances. The methods of application, such as spraying, atomizing, dusting, scattering or watering, are selected to suit the intended objectives and the given circumstances, as is the type of agent.

The formulation, i.e. the agents, preparations or compositions containing the active substance of the formulae I and/or IV, or combinations of these active substances with other insecticides or acaricides, and if desired a solid or liquid additive, are (sic) prepared in a known manner, for example by intimately mixing and- /or grinding the active substances with extenders, for example with solvents, solid carriers, and, if desired, surface-active compounds (surfactants).

Suitable solvents can be: aromatic hydrocarbons, preferably the $C_8$ to $C_{12}$ fractions, for example xylene mixtures or substituted naphthalenes, phthalic acid esters, such as dibutyl or dioctyl phthalate, aliphatic hydrocarbons, such as cyclohexane or paraffins, alcohols and glycols and also their ethers and esters, such as ethanol, ethylene glycol, ethylene glycol monomethyl ether or ethylene glycol monoethyl ether, ketones, such as cyclohexanone, strongly polar solvents, such as N-methyl-2-pyrrolidone, dimethyl sulfoxide or dimethylformamide, and epoxidized or non-epoxidized vegetable oils, such as epoxidized coconut oil or soybean oil, or water.

Solid carriers which are generally used, for example for dusts and dispersible powders, are ground natural minerals, such as calcite, talc, kaolin, montmorillonite or attapulgite. It is also possible to add highly-disperse silicas or highly-disperse absorptive polymers to improve the physical properties. Possible granulated, absorptive granule carriers are porous types, for example pumice, brick grit, sepiolite or bentonite, and possible non-sorptive carrier materials are for example calcite or sand. Moreover, a large number of materials of inorganic or organic origin in the form of granules, such as in particular dolomite or comminuted plant residues, can be used.

Suitable surface-active compounds, depending on the type of the active substance of the formulae I or IV to be formulated or on the combinations of these active substances with other insecticides or acaricides, are non-ionogenic, cation- and/or anion-active surfactants having good emulsifying, dispersing and wetting properties. Surfactants are also to be understood as meaning surfactant mixtures.

Suitable anionic surfactants can be both so-called water-soluble soaps and water-soluble, synthetic surface-active compounds.

As soaps, the alkali metal salts, alkaline earth metal salts or substituted or unsubstituted ammonium salts of higher fatty acids ($C_{10}$–$C_{22}$), for example the Na or K salts of oleic or stearic acid, or of natural mixtures of fatty acids which are obtained, for example, from coconut or tallow oil, are suitable. Other surfactants which may be mentioned are the fatty acid methyl-taurine salts and modified and non-modified phospholipids.

However, so-called synthetic surfactants are used more frequently, in particular fatty sulfonates, fatty sulfates, sulfonated benzimidazole derivatives or alkylarylsulfonates.

The fatty sulfonates or fatty sulfates are generally present in the form of alkali metal salts, alkaline earth metal salts or substituted or unsubstituted ammonium salts, and generally have an alkyl radical having 8 to 22 C atoms, alkyl also including the alkyl part of acyl radicals, for example the Na or Ca salt of ligninsulfonic acid, dodecylsulfuric acid ester or a fatty alcohol sulfate mixture prepared from natural fatty acids. These also include the salts of sulfuric acid esters and sulfonic acids of fatty alcohol/ethylene oxide adducts. The sulfonated benzimidazole derivatives preferably contain 2 sulfonic acid groups and one fatty acid radical having approximately 8–22 C atoms. Alkylarylsulfonates are, for example, the Na, Ca or triethanolamine salts of do- decylbenzenesulfonic acid, of dibutylnaphthalenesulfonic acid or of a naphthalenesulfonic acid/formaldehyde condensation product. Other suitable substances are corresponding phosphates, for example salts of the phosphoric acid ester of a p-nonylphenol (4-14)-ethylene oxide adduct.

Suitable non-ionic surfactants are mainly polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols. Other suitable non-ionic surfactants are the water-soluble polyethylene oxide adducts with polypropylene glycol, ethylene diaminopolypropylene glycol and alkyl polypropylene glycol having 1 to 10 carbon atoms in the alkyl chain, which surfactants contain 20 to 250 ethylene glycol ether groups and 10 to 100 propylene glycol ether groups. The mentioned compounds usually contain 1 to 5 ethylene glycol units per propylene glycol unit.

Examples which may be mentioned of non-ionic surfactants are nonylphenolpolyethoxyethanols, castor oil polyglycol ethers, castor oil thioxilate, polypropylene/-polyethylene oxide adducts, tributylphenoxypolyethoxyethanol, polyethylene glycol and octylphenoxypolyethoxyethanol. Other suitable substances are fatty acid esters of polyoxyethylene sorbitan, for example polyoxyethylene sorbitan trioleate.

The cationic surfactants are mainly quaternary ammonium salts, which contain at least one alkyl radical having 8 to 22 C atoms as N-substituent and lower, halogenated or non-halogenated alkyl, benzyl or lower hydroxyalkyl radicals as further substituents. The salts are preferably present in the form of halides, methyl sulfates or ethyl sulfates, for example stearyltrimethylammonium chloride or benzyldi(2-chloroethyl)ethylammonium bromide.

The surfactants which are conventionally used in the art of formulation are described, inter alia, in the following publications:

"1985 International Mc Cutcheon's Emulsifiers & Detergents", Glen Rock N.J. USA, 1985, "H. Stache, "Tensid-Taschenbuch [Pocket-Book of Surfactants]", 2nd Ed., C. Hanser Verlag Munich, Vienna 1981, M. and J. Ash. "Encyclopedia of Surfactants", Vol. I-III, Chemical Publishing Co., New York, 1980–1981.

The pesticidal preparations generally contain 0.1 to 99%, in particular 0.1 to 95%, of the (+)-enantiomer of the active substance of the formula I or combinations of this active substance with other insecticides or acaricides, 1 to 99.9% of a solid or liquid additive and 0 to 25%, in particular 0.1 to 20%, of a surfactant. Whereas concentrated agents are preferred as commercial products, the final consumer generally uses diluted preparations which show much lower concentrations of active substance. Typical application concentrations are between 0.1 and 1000 ppm, preferably between 0.1 and 500 ppm. The application rates per hectare are generally 1 to 1000 g of active substance per hectare, preferably 25 to 500 g/ha.

In particular, preferred formulations have the following compositions: (%=per cent by weight)

| Emulsifiable concentrates | |
|---|---|
| Active substance | 1 to 20%, preferably 5 to 10% |
| Surface-active agent | 5 to 30%, preferably 10 to 20% |
| Liquid carrier | 50 to 94%, preferably 70 to 85% |
| Dusts | |
| Active substance | 0.1 to 10%, preferably 0.1 to 1% |
| Solid carrier | 99.9 to 90%, preferably 99.9 to 99% |
| Suspension concentrates | |
| Active substance | 5 to 75%, preferably 10 to 50% |
| Water | 94 to 24%, preferably 88 to 30% |
| Surface-active agent | 1 to 40%, preferably 2 to 30% |
| Wettable powders | |
| Active substance | 0.5 to 90%, preferably 1 to 80% |
| Surface-active agent | 0.5 to 20%, preferably 1 to 15% |
| Solid carrier | 5 to 95%, preferably 15 to 90% |
| Granules | |
| Active substance | 0.5 to 30%, preferably 3 to 15% |
| Solid carrier | 99.5 to 70%, preferably 97 to 85% |

The agents can also contain further additives, such as stabilizers, defoamers, preservatives, viscosity regulators, binders, tackifiers and fertilizers and other active substances in order to obtain specific effects.

The examples which follow illustrate the invention but do not impose any restrictions.

EXAMPLE 1

Preparation

1.1. Intermediates

1.1.1.
N-[2,6-Diisopropyl-4-(2-fluorophenoxy)-phenyl]-N'-isopropyl-S-acetylisothiourea hydrochloride 7.7 g of N-[2,6-diisopropyl-4-(2-fluorophenoxy)-phenyl]-N'-isopropylthiourea are dissolved in 20 ml of acetone, and 2.36 g of acetyl chloride are added dropwise with stirring at +5° to 10° C. The reaction mixture is subsequently allowed to stand for 3 hours at +10° C. The product which has crystallized out is filtered off with suction, washed with a little acetone and dried in vacuo. The title compound of the formula

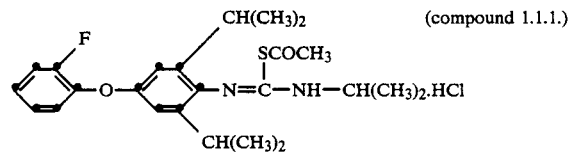

(compound 1.1.1.)

is present in the form of colourless crystals; melting point 164° C. with decomposition.

The following compounds are prepared analogously:

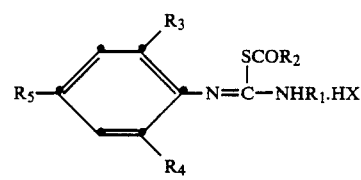

| Comp. No. | R$_1$ | R$_2$ | R$_3$ | R$_4$ | R$_5$ | X | M.p. °C. |
|---|---|---|---|---|---|---|---|
| 1.1.2. | C(CH$_3$)$_3$ | CH$_3$ | C$_2$H$_5$ | CH(CH$_3$)$_2$ | H | Cl | 124–128 |
| 1.1.3. | CH(CH$_3$)$_2$ | CH$_3$ | C$_2$H$_5$ | CH(CH$_3$)$_2$ | H | Cl | 159–161 |
| 1.1.4. | C(CH$_3$)$_3$ |  | C$_2$H$_5$ | C$_2$H$_5$ | H | Cl | 130 |

-continued

| Comp. No. | R₁ | R₂ | R₃ | R₄ | R₅ | X | M.p. °C. |
|---|---|---|---|---|---|---|---|
| | C(CH₃)₃ | CH₃ | CH(CH₃)₂ | CH(CH₃)₂ | H | Cl | |
| | C(CH₃)₃ | CH₃ | CH(CH₃)₂ | CH(CH₃)₂ | phenyl-O— | Cl | |
| | CH(CH₃)₂ | CH(CH₃)₂ | C₂H₅ | CH(CH₃)₂ | H | Cl | |
| | CH(CH₃)₂ | phenyl | C₂H₅ | CH(CH₃)₂ | H | Cl | |
| | CH(CH₃)₂ | CH₃ | CH(CH₃)₂ | CH(CH₃)₂ | phenyl-N(CH₃)— | Cl | |
| | CH(CH₃)₂ | CH₃ | CH(CH₃)₂ | CH(CH₃)₂ | CH₃S— | Cl | |
| | CH(CH₃)₂ | CH₃ | CH(CH₃)₂ | CH(CH₃)₂ | CH₃SO₂— | Cl | |
| | CH(CH₃)₂ | CH₃ | CH(CH₃)₂ | CH(CH₃)₂ | F-phenyl-N(CH₃)— | Cl | |
| | CH(CH₃)₂ | CH₃ | Cyclopentyl | CH(CH₃)₂ | H | Cl | |
| | CH(CH₃)₂ | CH₃ | Cyclopentyl | C₂H₅ | H | Cl | |
| | CH(CH₃)₃ | CH(CH₃)₂ | Cyclopentyl | CH(CH₃)₂ | H | Cl | |
| | CH(CH₃)₂ | CH₃ | CH(CH₃)₂ | CH(CH₃)₂ | phenyl-CH₂— | Cl | |

1.2. End products

1.2.1.
N-(2-Ethyl-6-isopropylphenyl)-N-acetyl-N'-tert-butyl-thiourea 9.75 g of N-(2-ethyl-6-isopropylphenyl)-N'-tert-butyl-thiourea, 3.55 g of triethylamine and 0.2 g of 4-dimethylaminopyridine are dissolved in 50 ml of acetone, and 2.75 g of acetyl chloride are added dropwise and with stirring at 0° to +5° C. Stirring of the reaction mixture is subsequently continued for one hour at 0° to +5° C., the mixture is then filtered, and the residue is washed with acetone. The acetone is removed from the filtrate by distillation, and the residue which has formed is purified on silica gel by means of chromatography, using a hexane/methylene chloride mixture. The title compound of the formula

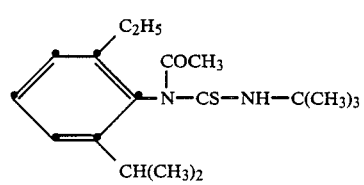

(compound 1.2.1.)

is present in the form of a pale yellow oil; refractive index n_D²⁴: 1.5379.

1.2.2.
N-[2,6-Diisopropyl-4-(2-fluorophenoxy)phenyl]-N-acetyl-N'-isopropylthiourea 3.1 g of N-[2,6-diisopropyl-4-(2-fluorophenoxy)phenyl]-N'-isopropyl-S-acetylisothiourea hydrochloride are suspended in 60 ml of acetone and 10 ml of water, and the suspension is stirred at room temperature for 24 hours. The reaction mixture is subsequently concentrated, and the residue is recrystallized from hexane. The title compound of the formula

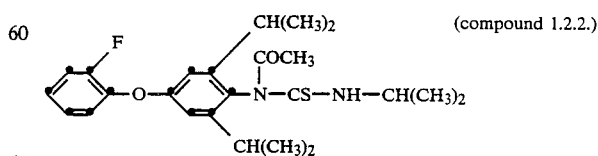

(compound 1.2.2.)

is present form of colourless crystals; melting point 122°–126° C.

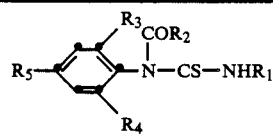

| Comp. No. | $R_1$ | $R_2$ | $R_3$ | $R_4$ | $R_5$ | Phys. data |
|---|---|---|---|---|---|---|
| 1.2.3. | $CH(CH_3)_2$ | $CH_3$ | $CH(CH_3)_2$ | $CH(CH_3)_2$ | H | m.p. 85–88° C. |
| 1.2.4. | $CH(CH_3)_2$ | $CH_3$ | $C_2H_5$ | $CH(CH_3)_2$ | H | $n_D^{24}$: 1,5492 |
| 1.2.5. | $CH(CH_3)_2$ | $CH_3$ | $C_2H_5$ | $CH(CH_3)C_2H_5$ | ⟨phenyl⟩-O— | $n_D^{24}$: 1,5632 |
| 1.2.6. | $CH(CH_3)_2$ | $CH(CH_3)_2$ | $C_2H_5$ | $CH(CH_3)_2$ | H | $n_D^{25}$: 1,5440 |
| 1.2.7. | $CH(CH_3)_2$ | $C_2H_5$ | $C_2H_5$ | $CH(CH_3)_2$ | H | m.p. 69–71° C. |
| 1.2.8. | $CH(CH_3)_2$ | ⟨phenyl⟩ | $C_2H_5$ | $CH(CH_3)_2$ | H | m.p. 78–80° C. |
| 1.2.9. | $CH(CH_3)_2$ | $CH_3$ | $C_2H_5$ | $CH(CH_3)_2$ | ⟨phenyl⟩-O— | m.p. 61–63° C. |
| 1.2.10. | $CH(CH_3)_2$ | $CH_3$ | $C_2H_5$ | $CH(CH_3)C_2H_5$ | H | $n_D^{24}$: 1,5459 |
| 1.2.11. | $CH(CH_3)_2$ | $CH_3$ | $C_2H_5$ | $C_2H_5$ | H | $n_D^{23}$: 1,5562 |
| 1.2.12. | $CH(CH_3)_2$ | ⟨phenyl⟩ | $C_2H_5$ | $C_2H_5$ | H | m.p. 60–62° C. |
| 1.2.13. | $CH(CH_3)C_2H_5$ | $CH_3$ | $C_2H_5$ | $CH(CH_3)_2$ | H | $n_D^{23}$: 1,5452 |
| 1.2.14. | $CH(CH_3)_2$ | $CH_3$ | $CH(CH_3)_2$ | $CH(CH_3)_2$ | F-⟨phenyl⟩-N(CH_3)— | m.p. 124–126° C. |
| 1.2.15. | $CH(CH_3)_2$ | $CH_3$ | $CH(CH_3)_2$ | $CH(CH_3)_2$ | $(CH_3)_2CH—S—$ | m.p. 84–86° C. |
| 1.2.16. | $CH(CH_3)_2$ | $CH_3$ | $CH(CH_3)_2$ | $CH(CH_3)_2$ | ⟨phenyl⟩-CH_2— | m.p. 83.5–85° C. |
| | $C(CH_3)_3$ | $CH_3$ | $CH(CH_3)_2$ | $CH(CH_3)_2$ | F-⟨phenyl⟩-O— | |
| | $C(CH_3)_3$ | $CH_3$ | $CH(CH_3)_2$ | $CH(CH_3)_2$ | H | |
| | $C(CH_3)_3$ | $CH_3$ | $CH(CH_3)_2$ | $CH(CH_3)_2$ | ⟨phenyl⟩-O— | |
| | $C(CH_3)_3$ | $CH_3$ | $C_2H_5$ | $CH(CH_3)C_2H_5$ | H | |
| | $C(CH_3)_3$ | $CH_3$ | $CH_3$ | $CH(CH_3)_2$ | H | |
| | $C(CH_3)_3$ | $CH_3$ | $CH_3$ | $C(CH_3)_3$ | H | |
| | $C(CH_3)_3$ | $CH_3$ | $CH(CH_3)_2$ | $CH(CH_3)_2$ | F,F-⟨phenyl⟩-O— | |
| | —$C(CH_3)_2$-⟨phenyl⟩ | $CH_3$ | $C_2H_5$ | $CH(CH_3)_2$ | H | |
| | $CH(CH_3)_2$ | —$CH_2$—$CH$=$CH_2$ | $C_2H_5$ | $CH(CH_3)_2$ | H | |
| | $CH(CH_3)_2$ | —$CH_2$-⟨phenyl⟩ | $C_2H_5$ | $CH(CH_3)_2$ | H | |
| | $CH(CH_3)_2$ | —$(CH_2)_4CH_3$ | $C_2H_5$ | $CH(CH_3)_2$ | H | |

-continued

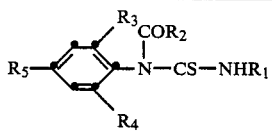

| Comp. No. | R₁ | R₂ | R₃ | R₄ | R₅ | Phys. data |
|---|---|---|---|---|---|---|
| | CH(CH$_3$)$_2$ | CH$_3$ | CH(CH$_3$)$_2$ | CH(CH$_3$)$_2$ | C$_6$H$_5$—O— | |
| | CH(CH$_3$)$_2$ | CH$_3$ | CH$_3$ | CH(CH$_3$)$_2$ | H | |
| | CH(CH$_3$)$_2$ | CH$_3$ | C$_2$H$_5$ | CH(CH$_3$)$_2$ | 2-CH$_3$-C$_6$H$_4$—O— | |
| | CH(CH$_3$)$_2$ | CH$_3$ | CH(CH$_3$)$_2$ | CH(CH$_3$)$_2$ | C$_6$H$_5$—N(CH$_3$)— | |
| | CH(CH$_3$)$_2$ | CH$_3$ | OCH(CH$_3$)$_2$ | CH(CH$_3$)$_2$ | CH(CH$_3$)$_2$ | |
| | CH(CH$_3$)$_2$ | CH$_3$ | CH(CH$_3$)$_2$ | CH(CH$_3$)$_2$ | CH$_3$S— | |
| | CH(CH$_3$)$_2$ | CH$_3$ | CH(CH$_3$)$_2$ | CH(CH$_3$)$_2$ | C$_6$H$_5$—N(CH$_3$)— | |
| | CH(CH$_3$)$_2$ | CH$_3$ | CH(CH$_3$)$_2$ | CH(CH$_3$)$_2$ | CH$_3$SO$_2$— | |
| | CH(CH$_3$)$_2$ | CH$_3$ | OCH(CH$_3$)$_2$ | CH$_3$ | CH$_3$ | |
| | CH(CH$_3$)$_2$ | CH$_3$ | CH(CH$_3$)$_2$ | CH(CH$_3$)$_2$ | (CH$_3$)$_2$CHO— | |
| | CH(CH$_3$)$_2$ | CH$_3$ | CH(CH$_3$)$_2$ | CH(CH$_3$)$_2$ | 4-Cl-C$_6$H$_4$—N(CH$_3$)— | |
| | CH(CH$_3$)$_2$ | CH$_3$ | CH(CH$_3$)$_2$ | CH(CH$_3$)$_2$ | C$_6$H$_5$—N(CHO)— | |
| | CH(CH$_3$)$_2$ | CH$_3$ | 2-Cyclopentenyl | CH(CH$_3$)$_2$ | H | |
| | CH(CH$_3$)$_2$ | CH$_3$ | CH(CH$_3$)$_2$ | CH(CH$_3$)$_2$ | CH(CH$_3$)$_2$ | |
| | CH(CH$_3$)$_2$ | CH$_3$ | Cyclopentyl | CH(CH$_3$)$_2$ | C$_6$H$_5$—O— | |
| | CH(CH$_3$)$_2$ | CH$_3$ | Cyclopentyl | CH(CH$_3$)$_2$ | H | |
| | CH(CH$_3$)$_2$ | CH$_3$ | CH(CH$_3$)$_2$ | CH(CH$_3$)$_2$ | CH$_3$ | |

1.3.1.
N-(2,6-Diisopropyl-4-phenoxyphenyl)-N-ethoxycarbonyl-N'-isopropylthiourea 13 g of N-(2,6-diisopropyl)-4-phenoxyphenyl)-N'-isopropylthiourea, 6.4 ml of triethylamine and 0.1 g of 4-dimethylaminopyridine are dissolved in 80 ml of acetone, and 6.5 g of ethyl chloroformate are added dropwise and with stirring at 0° to +5° C. Stirring of the reaction mixture is subsequently continued for 10 hours at 0° to +5° C., the mixture is then filtered, and the filtrate is concentrated on a rotary evaporator. The crude product is purified by chromatography on a silica gel column, using a 10:1 hexane/methylene chloride mixture. The title compound of the formula

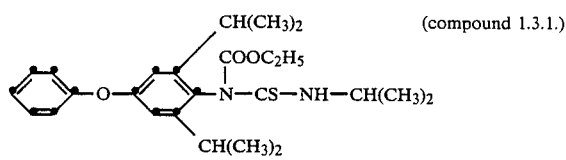

(compound 1.3.1.)

is present in the form of colourless crystals; melting point 107°–108° C.

The following compounds are prepared analogously:

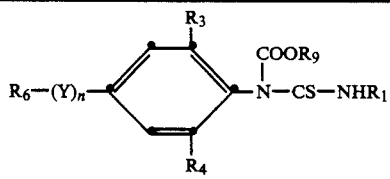

| Comp. No. | $R_1$ | $R_9$ | $R_3$ | $R_4$ | $R_6(Y)_n$ | Phys. data |
|---|---|---|---|---|---|---|
| 1.3.2. | $CH(CH_3)_2$ | $C_2H_5$ | $CH(CH_3)_2$ | $CH(CH_3)_2$ | 2-F-C6H4-O— | m.p. 117–119° C. |
| 1.3.3. | $CH(CH_3)_2$ | $C_2H_5$ | $CH(CH)_2$ | $CH(CH_3)_2$ | C6H5-S— | m.p. 88–90° C. |
| 1.3.4. | $CH(CH_3)_2$ | $C_2H_5$ | $CH_3$ | $CH(CH_3)_2$ | C6H5-O— | $n_D^{25}$: 1.5508 |
| 1.3.5. | $CH(CH_3)_2$ | $C_2H_5$ | $C_2H_5$ | $CH(CH_3)C_2H_5$ | C6H5-O— | $n_D^{22}$: 1.5482 |
| 1.3.6. | $CH(CH_3)_2$ | $C_2H_5$ | $C_2H_5$ | $C_2H_5$ | C6H5-O— | $n_D^{22}$: 1.5623 |
| 1.3.7. | $CH_2-C(CH_3)_3$ | $C_2H_5$ | $CH(CH_3)_2$ | $CH(CH_3)_2$ | C6H5-O— | $n_D^{23}$: 1.5392 |
| 1.3.8. | $CH(CH_3)_2$ | $C_2H_5$ | $CH(CH_3)_2$ | $CH(CH_3)_2$ | C6H5-N(CHO)— | m.p. 176° C. |
| 1.3.9. | $CH(CH_3)_2$ | $C_2H_5$ | $CH(CH_3)_2$ | $CH(CH_3)_2$ | 3-F-C6H4-N(CH3)— | m.p. 140–142° C. |
| 1.3.10. | $CH(CH_3)C_2H_5$ | $C_2H_5$ | $C_2H_5$ | $CH(CH_3)_2$ | C6H5-O— | $n_D^{27}$: 1.5531 |
|  | $CH(CH_3)_2$ | $C_2H_5$ | $CH(CH_3)_2$ | $CH(CH_3)_2$ | 2-F,4-F-C6H3-O— |  |
|  | $CH(CH_3)_2$ | $CH_3$ | $CH(CH_3)_2$ | $CH(CH_3)_2$ | C6H5-O— |  |

-continued

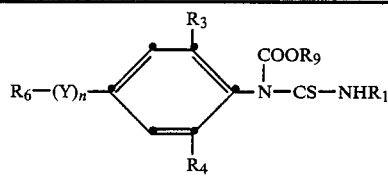

| Comp. No. | R₁ | R₉ | R₃ | R₄ | R₆(Y)ₙ | Phys. data |
|---|---|---|---|---|---|---|
| | CH(CH₃)₂ | C₃H₇ | CH(CH₃)₂ | CH(CH₃)₂ | C₆H₅—O— | |
| | CH(CH₃)₂ | C₄H₉ | CH(CH₃)₂ | CH(CH₃)₂ | C₆H₅—O— | |
| | CH(CH₃)₂ | C₂H₅ | CH(CH₃)₂ | CH(CH₃)₂ | C₆H₅—CH₂— | |
| | CH(CH₃)₂ | C₂H₅ | C₂H₅ | CH(CH₃)₂ | C₆H₅—O— | |
| | CH(CH₃)₂ | C₂H₅ | CH(CH₃)₂ | CH(CH₃)₂ | C₆H₅—N(CH₃)— | |
| | C(CH₃)₃ | C₂H₅ | CH(CH₃)₂ | CH(CH₃)₂ | C₆H₅—O— | |
| | C(CH₃)₃ | C₂H₅ | CH₃ | CH(CH₃)₂ | C₆H₅—O— | |

EXAMPLE 2

Formulations of active substances of the formulae I and IV according to Preparation Examples 1.1. and 1.2. and 1.3. (%=per cent by weight)

2 1. Emulsion concentrates

| | (a) | (b) |
|---|---|---|
| Active substance according to Preparation Example 1.1. or 1.2. or 1.3. | 10% | 25% |
| Ca dodecylbenzenesulfonate | — | 5% |
| Castor oil polyethylene glycol ether (36 mol of EO) | 25% | 5% |
| Cyclohexanone | — | 40% |
| Butanol | 15% | — |
| Xylene mixture | — | 25% |
| Ethyl acetate | 50% | — |

Emulsions of any desired concentration can be prepared from such concentrates by dilution with water.

2.2. Solutions

| | (a) | (b) |
|---|---|---|
| Active substance according to Preparation Example 1.1. or 1.2. or 1.3. | 10% | 5% |
| Polyethylene glycol (MW 400) | 70% | — |
| N-Methyl-2-pyrrolidone | 20% | 20% |
| Epoxidized coconut oil | — | 1% |
| Benzine (boiling range 160–190° C.) | — | 74% |

The solutions are suitable for application in the form of very small drops.

2.3. Granules

| | (a) | (b) |
|---|---|---|
| Active substance according to Preparation Example 1.1. or 1.2. or 1.3. | 5% | 10% |
| Kaolin | 94% | — |
| Highly disperse silica | 1% | — |

-continued

|  | (a) | (b) |
|---|---|---|
| Attapulgite | — | 90% |

The active substance is dissolved in methylene chloride, the solution sprayed onto the carrier, and the solvent is subsequently evaporated in vacuo.

2.4. Extruder granules

| Active substance according to Preparation Example 1.1. or 1.2. or 1.3. | 10% |
|---|---|
| Na ligninsulfonate | 2% |
| Carboxymethylcellulose | 1% |
| Kaolin | 87% |

The active substance is mixed with the additives, and the mixture is ground and moistened with water. This mixture is extruded and subsequently dried in a stream of air.

2.5 Coated granules

| Active substance according to Preparation Example 1.1. or 1.2. or 1.3. | 3% |
|---|---|
| Polyethylene glycol (MW 200) | 3% |
| Kaolin | 94% |

Kaolin, which has been moistened with polyethylene glycol, is uniformly coated in a mixer with the finely-ground active substance. In this manner, dust-free coated granules are obtained.

2.6. Dusts

|  | (a) | (b) | (c) | (d) |
|---|---|---|---|---|
| Preparation Example 1.1. or 1.2. or 1.3. | 2% | 5% | 5% | 8% |
| Highly-disperse silica | 1% | 5% | — | — |
| Talc | 97% | — | 95% | — |
| Kaolin | — | 90% | — | 92% |

Ready-for-use dusts are obtained by intimately mixing the carriers wit the active substance and, if desired, grinding the mixture on a suitable mill.

2.7 Wettable powders

|  | (a) | (b) | (c) |
|---|---|---|---|
| Active substance according to Preparation Example 1.1. or 1.2. or 1.3. | 20% | 50% | 75% |
| Na ligninsulfonate | 5% | 5% | — |
| Na lauryl sulfate | 3% | — | 5% |
| Na diisobutylnaphthalene sulfonate | — | 6% | 10% |
| Octylphenol polyethylene glycol ether (7-8 mol of EO) | — | 2% | — |
| Highly-disperse silica | 5% | 10% | 10% |
| Kaolin | 67% | 27% | — |

The active substance is thoroughly mixed with the additives, and the mixture is ground in a suitable mill. Wettable powders are obtained which can be diluted with water to give suspensions of any desired concentration.

2.8. Suspension concentrate

| Active substance according to | 40% |
|---|---|
| Ethylene glycol | 10% |
| Nonylphenol polyethylene glycol ether (15 mol of EO) | 6% |
| Na ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely-ground active substance is intimately mixed with the additives. In this manner, a suspension concentrate is obtained from which suspensions of any desired concentration can be prepared by dilution with water.

EXAMPLE 3

Biological tests 3.1. Action against bluebottles

Small portions (30 to 50 eggs) of freshly laid eggs of the bluebottle species Lucilia sericata are transferred to test tubes in which 4 ml of nutrient medium were previously mixed with 1 ml of test solution containing 80 ppm of the active substance to be tested. After the culture medium has been inoculated, the test tubes are sealed with a cottonwool plug and incubated for 4 days in an incubator at 30° C. Up to this point in time, larvae of approx. length 1 cm have developed in the untreated medium (stage 3). If the substance is active, the larvae are either dead at this point in time or clearly underdeveloped. The evaluation is carried out after 96 hours; the mortality is determined as a percentage. In this test, compounds according to Examples 1.1. and 1.2. and 1.3. show a good action against *Lucilia sericata*.

3.2. Action against *Aedes aegypti*

An amount of a 0.1% acetone solution of the active substance is pipetted onto the surface of 150 ml of water in a container such that a concentration of 12.5 ppm is obtained. After the acetone has evaporated, 30-40 2-day-old Aedes larvae are inserted into the container. The mortality is checked after 2 and 7 days.

Compounds according to Examples 1.1. and 1.2. and 1.3. show a good action in this test.

3.3. Stomach-poison action on *Spodoptera littoralis* larvae ($L_1$)

Cotton plants in the cotyledon stage are sprayed with an aqueous emulsion of active substance (obtained from a 10% emulsifiable concentrate), the emulsion of active substance containing 400 ppm of the compound to be tested.

After the coating has dried on, each cotton plant is infested with *Spodoptera littoralis* larvae in the first larval stage. The experiment is carried out at 26° C. and approx. 50% relative atmospheric humidity. Mortality and disturbances in development and ecdysis of the larvae are determined after 2 and 3 days.

Compounds according to Examples 1.1. and 1.2. and 1.3. show a good action in this test.

3.4. Action against phytopathogenic Acarina: *Tetranychus urticae* (OP sensitive) and *Tetranychus cinnabarinus* (OP tolerant)

16 hours before the acaricidal action is tested, a leaf segment infested with a mass rearing of *Tetranychus urticae* (OP sensitive) or *Tetranychus cinnabarinus* (OP tolerant) are placed on the primary leaves of *Phaseolus vulgaris* plants (the tolerance refers to the acceptability of diazinone).

The infested plants which have been treated in this manner are sprayed with a test solution containing 400 ppm of the respective compound to be tested, until dripping wet. After 24 hours, and again after 7 days, imagines and larvae (all mobile stages) are evaluated under a stereomicroscope for live and dead individuals. One plant is used per concentration and per test species. During the experiment, the plants stand in greenhouse compartments at 25° C.

In this experiment, compounds according to Examples 1.1. and 1.2. and 1.3. show a good action against Tetranychus urticae and against *Tetranychus cinnabarinus*.

3.5. Contact action against *Nephotettix cincticeps* (nymphae)

The test is carried out on growing plants, for which purpose approximately 20 day old rice plants of an approximate height of 15 cm are planted in pots (diameter 5.5 cm).

On a rotating plate, each of the plants is sprayed with 100 ml of an acetonic solution containing 400 ppm of the active substance to be tested. After the spray coating has dried on, the infestation of each plant is carried out using in each case 20 nymphs of the test animals in the second or third stage. In order to prevent the leaf hoppers from escaping, a plexiglass cylinder is put over each infested plant and covered with gauze. The nymphs are kept on the treated plant for 5 days, and the plant must be rewatered at least once. The experiment is carried out at a temperature of approximately 23° C., at 55% relative atmospheric humidity and with an illumination period of 16 hours.

In this test, compounds according to Examples 1.1. and 1.2. and 1.3. show a good action.

3.6. Contact action against *Nilaparvata lugens* (nymphs)

The test is carried out on growing plants, for which purpose approximately 20 day old rice plants of an approximate height of 15 cm are planted in pots (diameter 5.5 cm).

On a rotating plate, each of the plants is sprayed with 100 ml of an acetone solution containing 400 ppm of the active substance to be tested. After the spray coating has dried on, the infestation of each plant is carried out using in each case 20 nymphs of the test animals in the second or third stage. In order to prevent the leaf hoppers from escaping, a plexiglass cylinder is put over each infested plant and covered with gauze. The nymphs are kept on the treated plant for 5 days, and the plant must be rewatered at least once. The experiment is carried out at a temperature of approximately 23° C., at 55% relative atmospheric humidity and with an illumination period of 16 hours.

In this test, compounds according to Examples 1.1. and 1.2. and 1.3. show a good action.

3.7. Systemic action on *Nilaparvata lugens*

Rice plants which are approximately 10 days old (height approx. 10 cm) are placed in a plastic beaker containing 20 ml of an aqueous emulsion preparation of the active substance to be tested in a concentration of 100 ppm, and which is closed with a plastic lid provided with holes. The root of the rice plant is pushed through one hole of the plastic lid into the aqueous test preparation. The hole is then sealed with cottonwool in order to hold the plant in place and to eliminate the influence of the gas phase from the test preparation. The rice plant is then infested with 20 *Nilaparvata lugens* nymphs in the N 2 to N 3 stage and covered with a plastic cylinder. The experiment is carried out at 20° C. and 60% relative atmospheric humidity with an illumination period of 16 hours. After 5 days, the number of destroyed test animals is scored by comparing them with untreated controls. By doing this, it can be observed if the active substance which is taken up via the roots destroys the test animals on the upper parts of the plant.

In the above test, compounds according to Examples 1.1. and 1.2. and 1.3. shown an 80-100% action (mortality) against *Nilaparvata lugens*.

3.8. Action against soil insects (*Diabrotica balteata*)

350 ml of soil (consisting of 95% by volume of sand and 5% by volume of peat) are in each case mixed with 150 ml of aqueous emulsion preparations containing the active substance to be tested in a concentration of 400 ppm. Plastic beakers having a top diameter of approx. 10 cm are then partly filled with the soil which has been treated in this manner. 10 larvae of *Diabrotica balteata* in the third larval stage are inserted per beaker, four maize seedlings are planted, and the beakers are topped up with soil. The filled beakers are covered with plastic foil and kept at a temperature of approximately 22° C. Ten days after the experiment has been set up, the soil in the beakers is sieved, and the remaining larvae are checked with respect to their mortality.

In the above test, compounds according to Examples 1.1. and 1.2. and 1.3. show a good action.

EXAMPLE 3.9.

Action against *Plasmopara-viticola* on grapevines

Residual-protective action

Grapevine seedlings in the 4–5 leaf stage are sprayed with a spray liquor prepared with a wettable powder of the active substance (0.02% of active substance). After 24 hours, the treated plants are inoculated with a sporangia suspension of the fungus. Infection with the fungus is assessed after a 6 days' incubation at 95–100% relative atmospheric humidity and 20° C.

Compounds according to Examples 1.1. and 1.2. show a good effectiveness against Plasmopara. For example, the compound No. 1.2.13. reduces infection with Plasmopara to 0 to 5%. In contrast, untreated but inoculated control plants show an infection with Plasmopara of 100%.

EXAMPLE 3.10.

Action against *Dermanyssus gallinae*

2 to 3 ml of a solution containing of active substance and approximately 200 mites in various developmental stages are put into a glass vessel, the top of which is open. The container is subsequently sealed with a cottonwool plug, shaken for 10 minutes until the mites are completely wetted, and then briefly turned over so that the remaining test solution can be absorbed by the cottonwool. After 3 days, the mortality of the mites is determined by counting the dead individuals and indicated as a percentage.

In the above test, compounds according to Examples 1.1. and 1.2. and 1.3. show a good action.

EXAMPLE 3.11.

Action against ectoparasitic ticks 5 fresh *Boophilus microplus females* which have sucked themselves full are stuck dorsally onto a PVC plate in one row and covered with a cottonwool ball. 10 ml of the aqueous test solution are then poured over the test animals. The cottonwool ball is removed after one hour, and the ticks are dried overnight at 24° C. After drying, the ticks are kept for 4 weeks at 28° C. and 80% atmospheric humidity until oviposition is complete and until the larvae start hatching.

Each test substance is tested at a concentration of 125 ppm. The acaricidal effects can be seen either in the form of mortality or sterility of the female, or in the deposited eggs by blockage of the embryogenesis or the act of hatching. All substances are tested against two different tick strains, the OP-resistant strain BIARRA and the amidine-resistant strain ULAM.

In the above test, the compounds according to Examples 1.1. and 1.2. and 1.3. show a good action.

What is claimed is:

1. A compound of the formula I

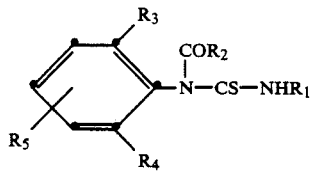

(I)

in which
R$_1$ is C$_1$–C$_{10}$alkyl, phenyl-C$_1$–C$_7$alkyl; C$_1$–C$_{10}$alkyl or phenyl-C$_1$–C$_7$alkyl each of which is monohalogenated or polyhalogenated or interrupted once or more than once by oxygen and/or sulfur; C$_3$–C$_8$cycloalkyl; C$_3$–C$_8$cycloalkyl which is monosubstituted or polysubstituted by halogen or C$_1$–C$_5$alkyl; or C$_3$–C$_8$cycloalkyl-C$_1$–C$_4$alkyl, R$_2$ is C$_1$–C$_{10}$alkyl, C$_2$–C$_{10}$alkenyl, C$_2$–C$_{10}$alkynyl, phenyl, phenyl-C$_1$–C$_7$alkyl, C$_3$–C$_8$cycloalkyl; C$_1$–C$_{10}$alkyl, C$_2$–C$_{10}$alkenyl, C$_2$–C$_{10}$alkynyl or phenyl-C$_1$–C$_7$alkyl each of which is monohalogenated or polyhalogenated or interrupted once or more than once by oxygen and/or sulfur; C$_3$–C$_8$cycloalkyl; phenyl or C$_3$–C$_8$cycloalkyl each of which is monosubstituted or polysubstituted by halogen or C$_1$–C$_5$alkyl; or is a radical —OR$_9$;

R$_3$ is C$_1$–C$_{10}$alkyl, C$_1$–C$_{10}$alkoxy, C$_3$–C$_7$cycloalkyl or C$_5$–C$_6$cycloalkenyl;

R$_4$ is C$_1$–C$_{10}$alkyl, C$_3$–C$_7$cycloalkyl or C$_5$–C$_6$cycloalkenyl;

R$_5$ is hydrogen or R$_6$(Y)$_n$;

R$_6$ is C$_1$–C$_{10}$alkyl, phenyl, naphthyl, indanyl, tetrahydronaphthyl; or phenyl, naphthyl, indanyl or tetrahydronaphthyl each of which is monosubstituted or polysubstituted by halogen, C$_1$–C$_4$alkyl, C$_1$–C$_4$alkoxy, C$_1$–C$_4$haloalkyl or C$_1$–C$_4$haloalkoxy;

R$_9$ is C$_1$–C$_{10}$alkyl, C$_3$–C$_{10}$alkenyl, C$_3$–C$_{10}$alkynyl, phenyl, phenyl-C$_1$–C$_7$alkyl, C$_3$–C$_8$cycloalkyl; C$_1$–C$_{10}$alkyl, C$_3$–C$_{10}$alkenyl, C$_3$–C$_{10}$alkynyl, phenyl-C$_1$–C$_7$alkyl each of which is monohalogenated or polyhalogenated or interrupted once or more than once by oxygen and/or sulfur; or phenyl or C$_3$–C$_8$cycloalkyl each of which is monosubstituted or polysubstituted by halogen or C$_1$–C$_5$alkyl;

Y is O, S, SO, SO$_2$, NH, N(CHO), N(CH$_3$) or C(R$_7$)R$_8$, where R$_7$ and R$_8$ each are hydrogen or C$_1$–C$_4$alkyl; and n is 0 or 1 with the proviso that R$_2$ can stand for the radical —OR$_9$ only when R$_5$ is other than hydrogen, C$_1$–C$_{10}$alkyl, C$_1$–C$_{10}$alkylthio and C$_1$–C$_{10}$alkoxy.

2. A compound according to claim 1, of the formula Ia

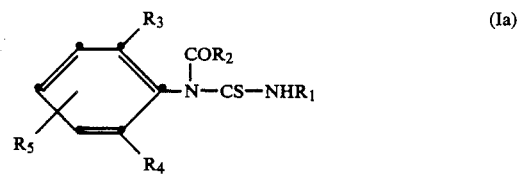

(Ia)

in which
R$_1$ is C$_1$–C$_{10}$alkyl, phenyl-C$_1$–C$_7$alkyl; C$_1$–C$_{10}$alkyl or phenyl-C$_1$–C$_7$alkyl each of which is monohalogenated or polyhalogenated or interrupted once or more than once by oxygen and/or sulfur; C$_3$–C$_8$cycloalkyl; or C$_3$–C$_8$cycloalkyl which is monosubstituted or polysubstituted by halogen or C$_1$–C$_5$alkyl;

R$_2$ is C$_1$–C$_{10}$alkyl, C$_2$–C$_{10}$alkenyl, C$_2$–C$_{10}$alkynyl, phenyl, phenyl-C$_1$–C$_7$alkyl, or is C$_1$–C$_{10}$alkyl, C$_2$–C$_{10}$alkenyl, C$_2$–C$_{10}$alkynyl or phenyl-C$_1$–C$_7$alkyl each of which is monohalogenated or polyhalogenated or interrupted once or more than once by oxygen and/or sulfur; C$_3$–C$_8$cycloalkyl; or C$_3$–C$_8$cycloalkyl which is monosubstituted or polysubstituted by halogen or C$_1$–C$_5$alkyl;

R$_3$ is C$_1$–C$_{10}$alkyl, C$_1$–C$_{10}$alkoxy, C$_3$–C$_7$cycloalkyl or C$_5$–C$_6$cycloalkenyl;

R$_4$ is C$_1$–C$_{10}$alkyl, C$_3$–C$_7$cycloalkyl or C$_5$–C$_6$cycloalkenyl;

R$_5$ is hydrogen or R$_6$(Y)$_n$;

R$_6$ is C$_1$–C$_{10}$alkyl, phenyl, naphthyl, indanyl, tetrahydronaphthyl; or phenyl, naphthyl, indanyl or tetrahydronaphthyl each of which is monosubstituted or polysubstituted by halogen, C$_1$–C$_4$alkyl, C$_1$–C$_4$alkoxy, C$_1$–C$_4$haloalkyl or C$_1$–C$_4$haloalkoxy;

Y is O, S, SO, SO$_2$, NH, N(CHO), N(CH$_3$) or C(R$_7$)R$_8$, where R$_7$ and R$_8$ each are hydrogen or C$_1$–C$_4$alkyl; and n is 0 or 1.

3. A compound of the formula Ia according to claim 2, in which R$_1$ is C$_1$–C$_5$alkyl or phenyl-C$_1$–C$_3$alkyl; R$_2$ is C$_1$–C$_5$alkyl, C$_2$–C$_5$alkenyl, C$_2$–C$_5$alkynyl, phenyl or phenyl-C$_1$–C$_3$alkyl; R$_3$ is C$_1$–C$_5$alkyl, C$_1$–C$_5$alkoxy, cyclopentyl or cyclopentenyl; R$_4$ is C$_1$–C$_5$alkyl; R$_5$ is hydrogen or R$_6$(Y)$_n$; R$_6$ is C$_1$–C$_5$alkyl, phenyl, naphthyl or indanyl; or is phenyl, naphthyl or indanyl each of which is monosubstituted or polysubstituted by fluorine, chlorine or C$_1$–C$_3$alkyl; Y is O, S, SO$_2$, NH, N(CHO), N(CH$_3$) or C(R$_7$)R$_8$, where R$_7$ and R$_8$ each are hydrogen or methyl; and n is 0 or 1.

4. A compound of the formula Ia according to claim 3, in which R$_1$ is C$_3$–C$_5$alkyl or phenyl-C$_2$–C$_3$alkyl; R$_2$ is $C_1-C_3$alkyl or phenyl; $R_3$ is $C_1-C_4$alkyl, $C_1-C_4$alkoxy, cyclopentyl or cyclopentenyl; $R_4$ is $C_1-C_4$alkyl; $R_5$ is hydrogen or $R_6Y$ in the 4-position; $R_6$ is $C_1-C_4$alkyl, phenyl or phenyl which is substituted by 1 or 2 fluorine; and Y is O or S.

5. A compound according to claim 4, of the formulae:

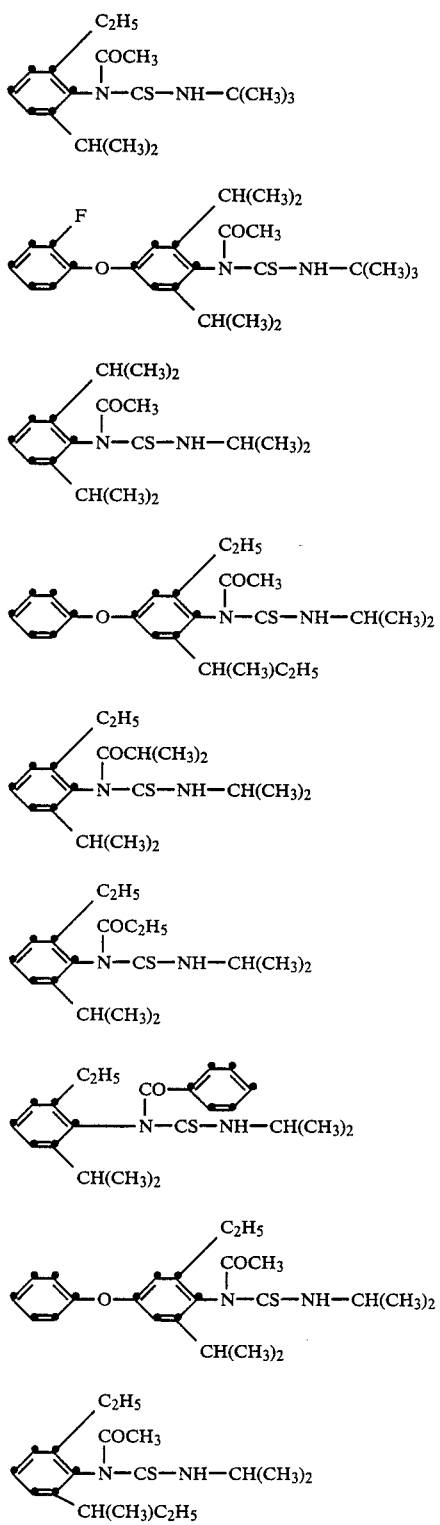

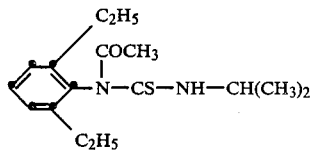

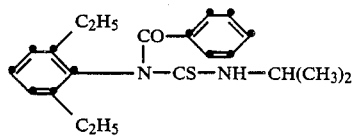

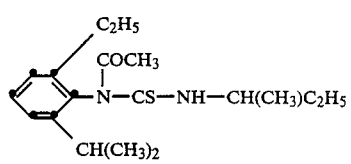

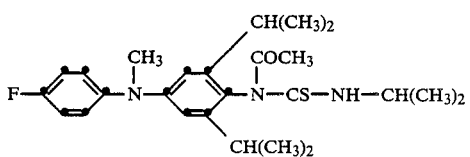

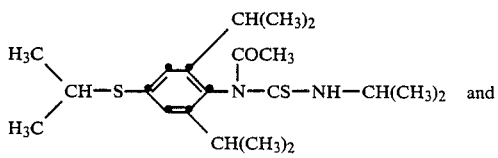

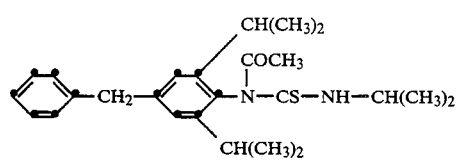

6. A compound according to claim 1, of the formula Ib

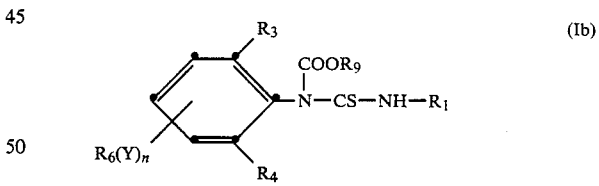

in which $R_1$ is $C_1-C_{10}$alkyl, phenyl-$C_1-C_7$alkyl; $C_1-C_{10}$alkyl or phenyl-$C_1-C_7$alkyl each of which is monohalogenated or polyhalogenated or interrupted once or more than once by oxygen and/or sulfur; $C_3-C_8$cycloalkyl; $C_3-C_8$cycloalkyl which is monosubstituted or polysubstituted by halogen or $C_1-C_5$alkyl; or $C_3-C_8$cycloalkyl-$C_1-C_4$alkyl;

$R_3$ is $C_1-C_{10}$alkyl, $C_1-C_{10}$alkoxy, $C_3-C_7$cycloalkyl or $C_5-C_6$cycloalkenyl;

$R_4$ is $C_1-C_{10}$alkyl, $C_3-C_7$cycloalkyl or $C_5-C_6$cycloalkenyl;

$R_6$ is phenyl, naphthyl, indanyl, tetrahydronaphthyl; or phenyl, naphthyl, indanyl or tetrahydronaphthyl each of which is monosubstituted or polysubstituted by halogen, $C_1$–$C_4$alkyl, $C_1$–$C_4$alkoxy, $C_1$–$C_4$haloalkyl or $C_1$–$C_4$haloalkoxy;

$R_9$ is $C_1$–$C_{10}$alkyl, $C_3$–$C_{10}$alkenyl, $C_3$–$C_{10}$alkynyl, phenyl, phenyl-$C_1$–$C_7$alkyl, $C_3$–$C_8$cycloalkyl; $C_1$–$C_{10}$alkyl, $C_3$–$C_{10}$alkenyl, $C_3$–$C_{10}$alkynyl, phenyl-$C_1$–$C_7$alkyl each of which is monohalogenated or polyhalogenated or interrupted once or more than once by oxygen and/or sulfur; or is phenyl or $C_3$–$C_8$cycloalkyl each of which is monosubstituted or polysubstituted by halogen or $C_1$–$C_5$alkyl;

Y is O, S, SO, $SO_2$, NH, N(CHO), N($CH_3$) or C($R_7$)$R_8$, where $R_7$ and $R_8$ each are hydrogen or $C_1$–$C_4$alkyl; and n is 0 or 1.

7. A compound of the formula Ib according to claim 6, in which $R_1$ is $C_1$–$C_5$alkyl or phenyl-$C_1$–$C_3$alkyl; $R_3$ is $C_1$–$C_5$alkyl, $C_1$–$C_8$alkoxy, cyclopentyl or cyclopentenyl; $R_4$ is $C_1$–$C_5$alkyl; $R_6$ is phenyl, naphthyl or indanyl: $R_9$ is $C_1$–$C_5$alkyl, $C_3$–$C_5$alkenyl, $C_3$–$C_5$alkynyl, phenyl or phenyl-$C_1$–$C_3$alkyl; Y is O, S, $SO_2$, NH, N(CHO) or C($R_7$)$R_8$, where $R_7$ and $R_8$ each are hydrogen or methyl; and n is 0 or 1.

8. A compound of the formula Ib according to claim 6, in which $R_1$ is $C_3$–$C_5$alkyl or phenyl-$C_2$–$C_3$alkyl; $R_3$ is $C_1$–$C_4$alkyl, $C_1$–$C_4$alkoxy or cyclopentyl; $R_4$ is $C_1$–$C_4$alkyl; $R_6$ is phenyl or phenyl which is substituted 1 or 2 fluorine; $R_9$ is $C_1$–$C_3$alkyl or pentyl; Y in the 4-position is O or S; and n is 1.

9. A compound according to claim 6, of the formulae

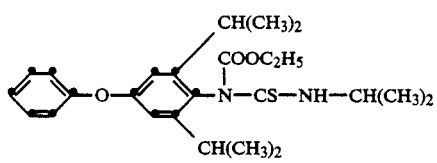
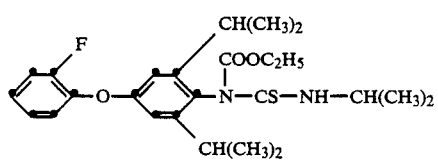
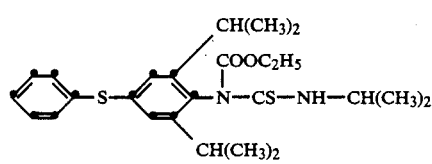
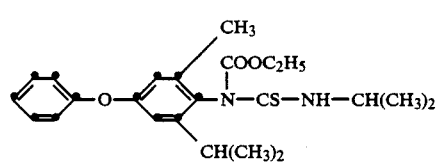
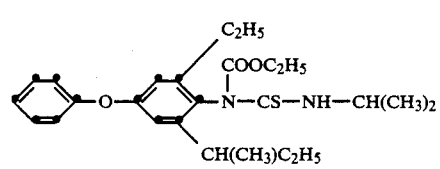

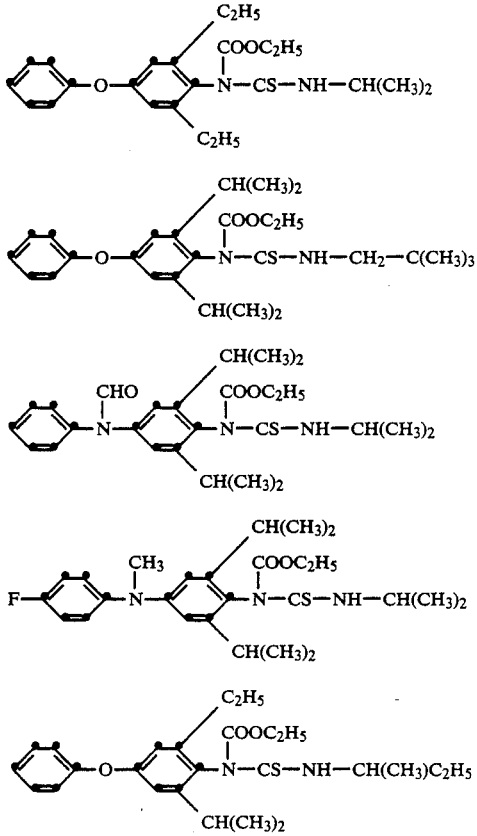

10. A pesticidal composition comprising as the active component, a pesticidally active amount of a compound of the formula

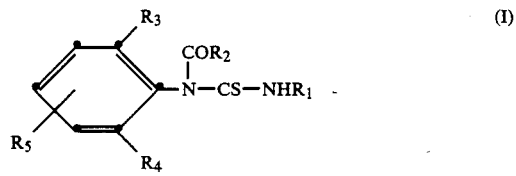

(I)

in which $R_1$ is $C_1$–$C_{10}$alkyl, phenyl-$C_1$–$C_7$alkyl; $C_1$–$C_{10}$alkyl or phenyl-$C_1$–$C_7$alkyl each of which is monohalogenated or polyhalogenated or interrupted once or more than once by oxygen and/or sulfur; $C_3$–$C_8$cycloalkyl $C_3$–$C_8$cycloalkyl which is monosubstituted or polysubstituted by halogen or $C_1$–$C_5$-alkyl; or $C_3$–$C_8$cycloalkyl-$C_1$–$C_4$alkyl, $R_2$ is $C_1$–$C_{10}$alkyl, $C_2$–$C_{10}$alkenyl, $C_2$–$C_{10}$alkynyl, phenyl, phenyl-$C_1$–$C_7$ alkyl, $C_3$–$C_8$cycloalkyl; $C_1$–$C_{10}$alkyl, $C_2$–$C_{10}$alkenyl, $C_2$–$C_{10}$alkynyl or phenyl-$C_1$–$C_7$alkyl each of which is monohalogenated or polyhalogenated or interrupted once or more than once by oxygen and/or sulfur; $C_3$–$C_8$cycloalkyl; phenyl or $C_3$–$C_8$cycloalkyl each of which is monosubstituted or polysubstituted by halogen or $C_1$–$C_5$alkyl; or is a radical —$OR_9$;

$R_3$ is $C_1$–$C_{10}$alkyl, $C_1$–$C_{10}$alkoxy, $C_3$–$C_7$cycloalkyl or $C_5$–$C_6$cycloalkenyl;

$R_4$ is $C_1$–$C_{10}$alkyl, $C_3$–$C_7$cycloalkyl or $C_5$–$C_6$cycloalkenyl;

$R_5$ is hydrogen or $R_6$(Y)$_n$;

$R_6$ is $C_1$-$C_{10}$alkyl, phenyl, naphthyl, indanyl, tetrahydronaphthyl; or phenyl, naphthyl, indanyl or tetrahydronaphthyl each of which is monosubstituted or polysubstituted by halogen, $C_1$-$C_4$alkyl, $C_1$-$C_4$alkoxy, $C_1$-$C_4$haloalkyl or $C_1$-$C_4$haloalkoxy;

$R_9$ is $C_1$-$C_{10}$alkyl, $C_3$-$C_{10}$alkenyl, $C_3$-$C_{10}$alkynyl, phenyl, phenyl-$C_1$-$C_7$-alkyl, $C_3$-$C_8$-cycloalkyl; $C_1$-$C_{10}$alkyl, $C_3$-$C_{10}$alkenyl, $C_3$-$C_{10}$alkynyl, phenyl-$C_1$-$C_7$alkyl each of which is monohalogenated or polyhalogenated or interrupted once or more than once by oxygen and/or sulfur; or phenyl or $C_3$-$C_8$cycloalkyl each of which is monosubstituted or polysubstituted by halogen or $C_1$-$C_5$alkyl;

Y is O, S, SO, $SO_2$, NH, N(CHO), N($CH_3$) or C($R_7$)$R_8$, where $R_7$ and $R_8$ each are hydrogen or $C_1$-$C_4$alkyl; and n is 0 or 1, with the proviso that $R_2$ can only be the radical —$OR_9$ when $R_5$ is other than hydrogen, $C_1$-$C_{10}$alkyl, $C_1$-$C_{10}$alkylthio or $C_1$-$C_{10}$alkoxy, together with a suitable carrier or other adjuvant.

* * * * *